US00PP27045P2

(12) United States Plant Patent

Klemm et al.

(10) Patent No.: US PP27,045 P2

(45) Date of Patent: Aug. 9, 2016

(54) *PETUNIA* PLANT NAMED 'KLEPH14245'

(50) Latin Name: *Petunia hybrida*
Varietal Denomination: KLEPH14245

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/545,074

(22) Filed: Mar. 23, 2015

(51) Int. Cl.
*A01H 5/02* (2006.01)

(52) U.S. Cl.
USPC ..... Plt./356.16

(58) Field of Classification Search
USPC ..... Plt./356.16
CPC ..... A01H 5/02
See application file for complete search history.

*Primary Examiner* — Kent L Bell

(74) *Attorney, Agent, or Firm* — Barbara Campbell; Bethany R. Roahrig; Cochran Freund & Young, LLC

(57) ABSTRACT

A new *petunia* plant particularly distinguished by having a violet-blue flower color and a semi-trailing plant habit, is disclosed.

1 Drawing Sheet

Genus and species: *Petunia hybrida.*
Variety denomination: 'KLEPH14245'.

BACKGROUND OF THE NEW PLANT

The present invention comprises a new and distinct variety of *petunia*, botanically known as *Petunia hybrida* and hereinafter referred to by the variety name 'KLEPH14245'. 'KLEPH14245' is a selection from a cross-pollination of the female *petunia* line 'PH-2001-U282' commercially known as variety 'Famous Light Blue' or 'U 282', also known as 'KLEC02061' (unpatented) and the commercial male *petunia* line Surfina Perfume Blue, also known as 'Sunsurblue' (patent status unknown).

In July of 2010 the proprietary female *petunia* line 'PH-2001-U282' and the proprietary male *petunia* line Surfina Perfume Blue were cross pollinated in Latina, Italy and seeds were obtained. The seeds were sown and plants were grown for evaluation. A plant line was selected in April 2011 in Latina, Italy and named 'KLEPH14245'. In April 2011, 'KLEPH14245' was first vegetatively propagated by terminal tip cuttings in Latina, Italy. 'KLEPH14245' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Violet-blue flower color; and
2. A semi-trailing plant habit.

DESCRIPTION OF THE PHOTOGRAPHS

This new *petunia* plant is illustrated by the accompanying photograph, which shows the plant grown in a pot. The plant is about 3 months-old grown in Stuttgart, Germany in May 2013.

The colors shown are as true as can be reasonably obtained by conventional photographic procedures.

DESCRIPTION OF THE NEW VARIETY

The following detailed descriptions set forth the distinctive characteristics of 'KLEPH14245'. The data which define these characteristics were collected from asexual reproductions carried out in Latina, Italy. Data was collected on twelve-week-old plants grown indoors in Latina, Italy under greenhouse conditions in February 2015. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH14245'.

Parentage:
- *Female.*—Commercial *petunia* line 'PH-2001-U282'.
- *Male.*—Commercial *petunia* line Surfina Perfume Blue also known as 'Sunsurblue'.

Plant:
- *Form.*—Vigorous growth.
- *Habit.*—Semi-trailing.
- *Height (from top of soil).*—5.0 cm.
- *Width (horizontal plant diameter).*—20.0 cm.
- *Propagation.*—Terminal tip cuttings.
- *Time to produce a finished flowering plant.*—About 14 weeks in winter under short day conditions, 7 weeks in spring.
- *Time to initiate and develop roots.*—2 to 3 weeks.
- *Root description.*—Moderate density, moderate branching, white roots.

Stems:
- *Average number (basal).*—11.
- *Length of basal branches (from the base of the stem to the tip).*—9.5 cm.
- *Internode length.*—0.8 cm to 1.5 cm.

*Diameter of branches* (*from midpoint*).—0.4 cm.
*Stem color*.—RHS 144D.
*Anthocyanin*.—Absent.
*Texture*.—Tomentose.

Leaves:
*Arrangement*.—Alternate.
*Length*.—4.3 cm.
*Width*.—2.2 cm.
*Shape*.—Elliptic.
*Apex*.—Broadly acuminate.
*Base*.—Attenuate.
*Margin*.—Entire.
*Immature leaf color*.—Upper surface: RHS 146A. Lower surface: RHS 146B. Mature leaf color: Upper surface: RHS 137B. Lower surface: RHS 146B. Texture: Upper and lower surfaces: Slightly pubescent. Venation pattern: Arcuate. Venation color: Upper and lower surfaces: RHS 145A. Petioles: Length: 0.5 cm. Diameter: 0.2 cm. Color: RHS 144C. Texture: Tomentose.

Flower bud:
*Shape*.—Irregular oblong.
*Length*.—3.5 cm to 4.3 cm.
*Diameter*.—0.5 cm.
*Color at tight bud*.—RHS 92A and RHS 145B.
*Texture*.—Slightly pubescent.

Inflorescence:
*Blooming habit* (*flowering season*).—Permanent flowering during summertime.
*Inflorescence type*.—Cymose.
*Number of flowers per node*.—2.
*Lastingness of individual blooms on the plant*.—7 to 10 days.
*Fragrance*.—Absent.
*Flowers*.—Arrangement: Composed of 5 petals fused at the base. Shape: Funnel form. Diameter (flower face): 5.5 cm. Depth (total length of flower): 6.0 cm. Throat/Funnel: Length: 2.5 cm. Diameter (at opening): 1.0 cm. Texture: Inner and outer surfaces: Smooth, glabrous. Color, immature flower: Face/Margin: Darker than RHS N88. Upper surface: Darker than RHS N88. Lower surface: RHS 90B. Color, mature flower: Face/Margin color: RHS 90C. Upper surface: RHS 90C. Lower surface: RHS 90D.
*Petals*.—Apex: Mucronate. Base: Fused. Margin: Entire. Strength of waviness: Weak. Degree of lobation: Medium weak.
*Calyx arrangement*.—Actinomorphic, composed of 5 sepals.
*Sepals*.—Color: Upper surface: RHS 146A. Lower surface: RHS 146B. Length: 1.2 cm. Width: 0.3 cm. Shape: Linear. Apex: Acute. Base: Attenuate. Margin: Entire. Texture: Upper and lower surfaces: Slightly pubescent.
*Pedicels*.—Color: RHS 144A. Length: 2.0 cm. Diameter: 0.1 cm. Texture: Pubescent.

Reproductive organs:
*Stamens*.—Quantity: 5. Shape: Needle like with elliptic head. Filament: Length: 1.8 cm to 2.2 cm. Diameter: 0.02 cm. Color: RHS 149D. Anther: Shape: Elliptic. Color: RHS N200D. Length: 0.25 cm. Diameter: 0.15 cm. Pollen: Color: RHS 156A. Amount: Moderate.
*Pistils*.—Quantity per flower: 1. Length: 2.2 cm. Stigma color: RHS 139B. Style color: RHS 145B.

Fruit and seed set: None observed.
Disease and pest/insect resistance: None observed.

COMPARISON WITH PARENTAL LINES AND KNOWN VARIETY

'KLEPH14245' is a distinct variety of *petunia*. 'KLEPH14245' is distinguished from its parents as described in Table 1:

TABLE 1

Comparison with Parental Lines

| Trait | Variety 'KLEPH14245' | Female parent 'PH-2001-U282' | Male Parent Surfina Perfume Blue |
|---|---|---|---|
| Flower color | Violet-blue | Purple-violet | Purple-violet |

'KLEPH14245' is most similar to the commercial *petunia* plant named Surfina Perfume Blue also known as 'Sunsurblue' (patent status unknown). Differences between the two varieties are described in Table 2:

TABLE 2

Comparison with Similar Variety

| Trait | Variety 'KLEPH14245' | Commercial line Surfina Perfume Blue |
|---|---|---|
| Flower color | Violet-blue | Purple-violet |

We claim:

1. A new and distinct variety of *petunia* plant named 'KLEPH14245' as illustrated and described herein.

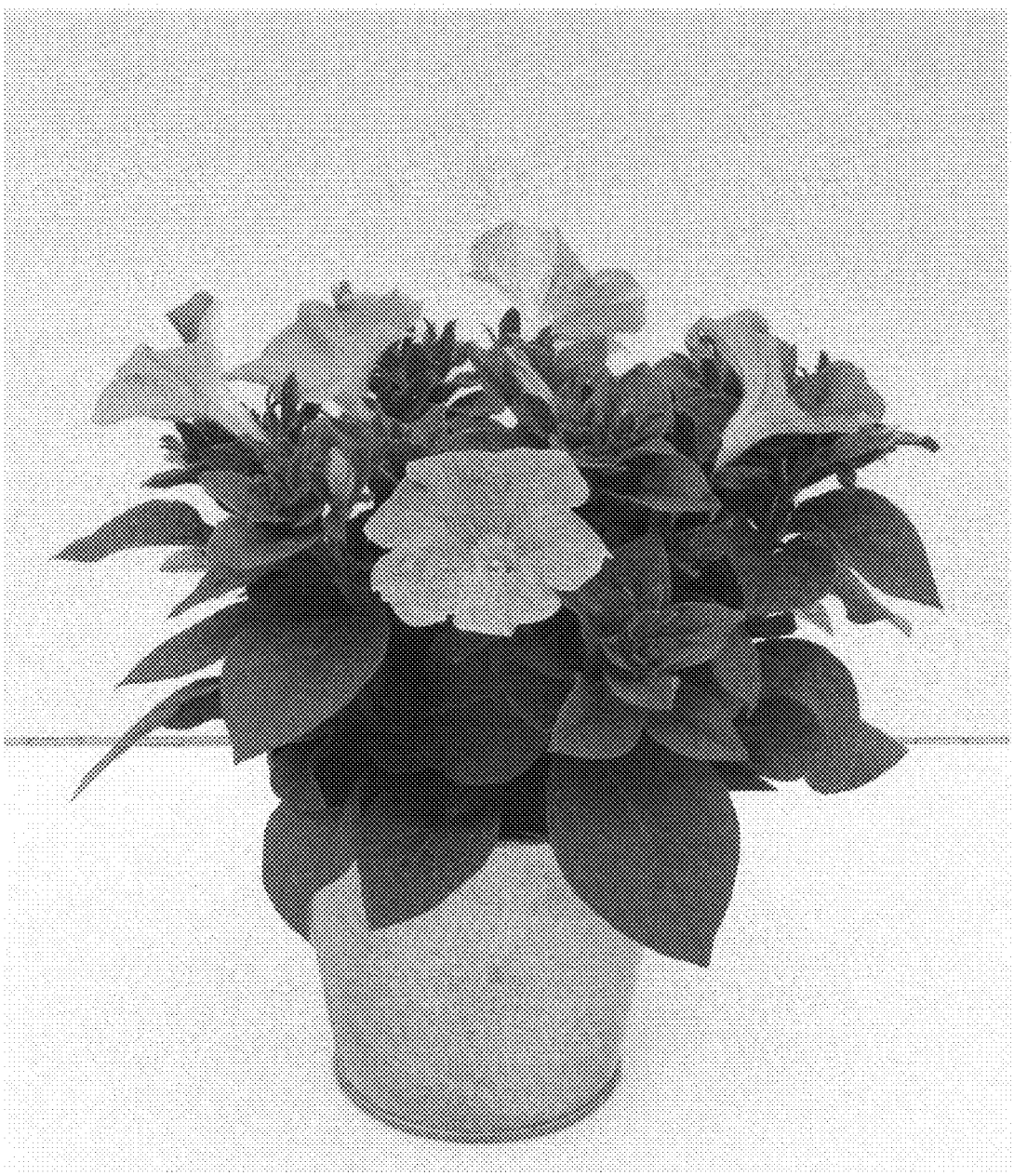

* * * * *